US012693278B2

(12) United States Patent (10) Patent No.: US 12,693,278 B2
Yamaguchi et al. (45) Date of Patent: Jul. 28, 2026

(54) GAS CONCENTRATION MEASUREMENT DEVICE

(71) Applicant: Murata Manufacturing Co., Ltd., Nagaokakyo (JP)

(72) Inventors: Yohei Yamaguchi, Nagaokakyo (JP); Masako Tenpaku, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 130 days.

(21) Appl. No.: 18/909,418

(22) Filed: Oct. 8, 2024

(65) Prior Publication Data

US 2025/0027921 A1      Jan. 23, 2025

Related U.S. Application Data

(63) Continuation of application No. PCT/JP2023/009654, filed on Mar. 13, 2023.

(30) Foreign Application Priority Data

Apr. 21, 2022     (JP) .................................. 2022-070044

(51) Int. Cl.
　　*G01N 33/00*　　　(2006.01)
　　*G01N 21/3504*　　(2014.01)
(52) U.S. Cl.
　　CPC ..... *G01N 33/0011* (2013.01); *G01N 21/3504* (2013.01)
(58) Field of Classification Search
　　CPC .................................................. G01N 33/0011
　　See application file for complete search history.

(56) References Cited

U.S. PATENT DOCUMENTS

| | | | |
|---|---|---|---|
| 5,608,167 | A | 3/1997 | Hale et al. |
| 8,252,250 | B2 | 8/2012 | Posner et al. |
| 8,597,594 | B2 | 12/2013 | Posner et al. |
| 8,753,584 | B2 | 6/2014 | Posner et al. |
| 9,772,293 | B2 | 9/2017 | Nakano et al. |
| 2010/0187115 | A1 | 7/2010 | Posner et al. |
| 2012/0292190 | A1 | 11/2012 | Posner et al. |

(Continued)

FOREIGN PATENT DOCUMENTS

| | | |
|---|---|---|
| JP | S61-218941 A | 9/1986 |
| JP | H08-505218 A | 6/1996 |

(Continued)

OTHER PUBLICATIONS

International Search Report received for PCT Patent Application No. PCT/JP2023/009654, mailed on May 16, 2023, 2 pages (English Translation Only).

*Primary Examiner* — Edwin C Gunberg
(74) *Attorney, Agent, or Firm* — ArentFox Schiff LLP

(57) ABSTRACT

A gas concentration measurement device that includes: a waterproof housing including a wall that defines an internal space, the wall including an opening communicating between the internal space and an outside of the housing; a measurement instrument in the internal space, the measurement instrument constructed to measure a concentration of a gas; a gas permeable membrane covering the opening, the gas permeable membrane allowing passage of the gas and substantially blocking passage of moisture; and a driving body constructed to vibrate the gas permeable membrane.

20 Claims, 10 Drawing Sheets

(56)       References Cited

U.S. PATENT DOCUMENTS

| | | |
|---|---|---|
| 2014/0080205 A1 | 3/2014 | Posner et al. |
| 2014/0197043 A1* | 7/2014 | Blomberg .......... G01N 33/0037 |
| | | 205/781 |
| 2015/0323468 A1 | 11/2015 | Nakano et al. |
| 2021/0210321 A1 | 7/2021 | Benavides Noriega et al. |
| 2022/0008023 A1* | 1/2022 | Kokubo ................. A61B 5/743 |
| 2022/0168670 A1* | 6/2022 | Plachetka .......... B01D 19/0036 |

FOREIGN PATENT DOCUMENTS

| | | |
|---|---|---|
| JP | H08-261984 A | 10/1996 |
| JP | 2006-090785 A | 4/2006 |
| JP | 2006-320849 A | 11/2006 |
| JP | 2008-180524 A | 8/2008 |
| JP | 2012-510063 A | 4/2012 |
| JP | 2014-126398 A | 7/2014 |

* cited by examiner

FIG. 2(A)
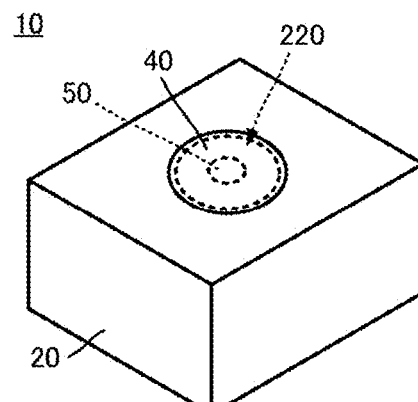
FIG. 2(B)
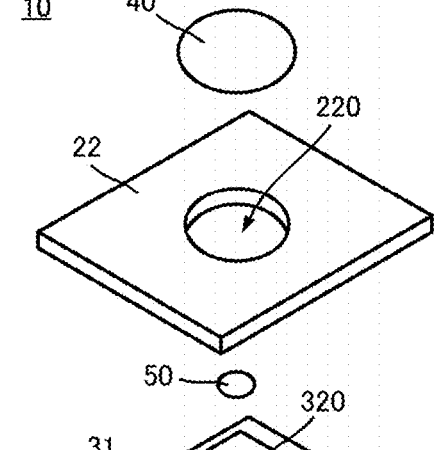
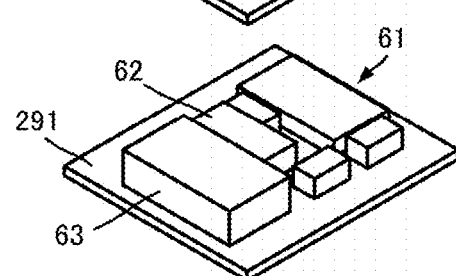
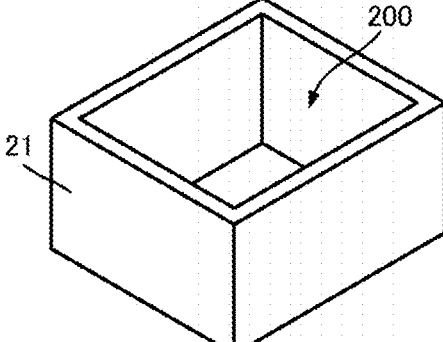

GAS CONCENTRATION MEASUREMENT DEVICE

CROSS REFERENCE TO RELATED APPLICATIONS

The present application is a continuation of International application No. PCT/JP2023/009654, filed Mar. 13, 2023, which claims priority to Japanese Patent Application No. 2022-070044, filed Apr. 21, 2022, the entire contents of each of which are incorporated herein by reference.

TECHNICAL FIELD

The present disclosure relates to a technology for measuring a gas concentration in a liquid, such as water.

BACKGROUND ART

Various sensors for measuring dissolved gases in water are currently being developed. For example, various sensors for measuring dissolved carbon dioxide in water are being developed for applications such as measuring the acidity of seawater, measuring the amount of carbon dioxide absorbed in seaweed beds, controlling the carbon dioxide concentration in the culture medium during algae cultivation, and detecting leaks in submarine carbon dioxide fixation ("Carbon Dioxide Capture and Storage," or "CCS").

For example, Patent Document 1 describes a measurement device for measuring the concentration of carbon dioxide dissolved in seawater. The measurement device according to Patent Document 1 includes a seawater tank, a pump, a measurement cell, and a pipe circuit.

The seawater tank, the pump, and the measurement cell are connected with the pipe circuit. The pump circulates the seawater in the seawater tank through the pipe circuit. Thus, the seawater is supplied to the measurement cell, and measurement cell measures the concentration of carbon dioxide contained in the seawater.

Patent Document 1: Japanese Unexamined Patent Application Publication (Translation of PCT Application) No. 8-505218

SUMMARY OF THE DISCLOSURE

However, the device according to Patent Document 1 needs to pump up the seawater, store the seawater in the tank, and circulate the seawater using the pump. Therefore, the device is large. In addition, the device described in Patent Document 1 cannot easily measure the gas to be measured.

Accordingly, an object of the present disclosure is to provide a small gas concentration measurement device capable of easily measuring the concentration of the gas to be measured.

A gas concentration measurement device according to the present disclosure includes: a waterproof housing including a wall that defines an internal space, the wall including an opening communicating between the internal space and an outside of the housing; a measurement instrument in the internal space, the measurement instrument constructed to measure a concentration of a gas; a gas permeable membrane covering the opening, the gas permeable membrane allowing passage of the gas and substantially blocking passage of moisture; and a driving body constructed to vibrate the gas permeable membrane.

According to this structure, gas dissolved in moisture is movable into the internal space of the housing through the gas permeable membrane, so that a gas equilibrium state (vapor-liquid equilibrium state) can be reached between the internal space of the housing and the moisture. Since the gas permeable membrane vibrates, the vapor-liquid equilibrium state can be reached in a shorter time. Thus, the gas concentration in the moisture can be measurement simply by placing the device in the water to be measured, and an increase in the size of the device can be suppressed because no tank or the like is required.

The present disclosure provides a small gas concentration measurement device capable of easily measuring the concentration of gas to be measured.

BRIEF DESCRIPTION OF THE DRAWINGS

FIG. 2(A) is an external perspective view of the gas concentration measurement device according to the first embodiment, and FIG. 2(B) is an exploded perspective view of the gas concentration measurement device according to the first embodiment.

FIGS. 4(A) and 4(B) are enlarged side sectional views of a gas permeable membrane during vibration.

FIGS. 11(A), 11(B), 11(C), and 11(D) are plan views illustrating various forms of driving bodies.

FIGS. 12(A), 12(B), and 12(C) are plan views illustrating various forms of housings and gas permeable membranes.

DESCRIPTION OF THE PREFERRED EMBODIMENTS

First Embodiment

Figure 1:
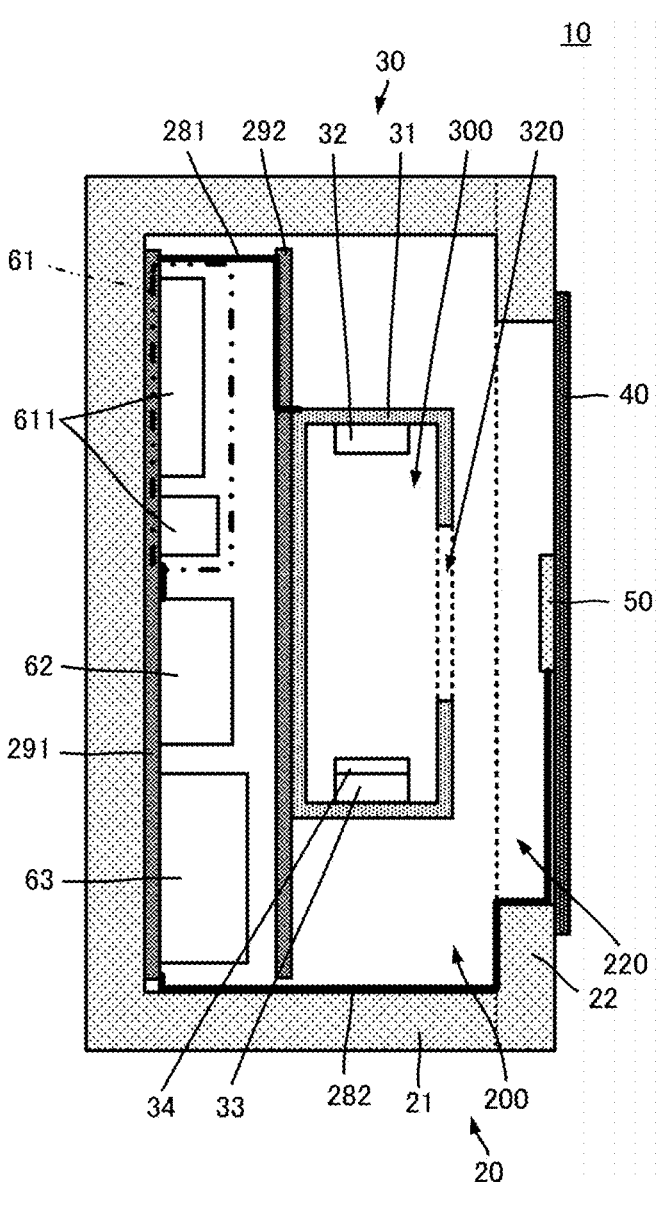
FIG. 1 is a sectional view illustrating the structure of a gas concentration measurement device according to a first embodiment.

A gas concentration measurement device according to a first embodiment of the present disclosure will be described with reference to the drawings. FIG. 1 is a sectional view illustrating the structure of the gas concentration measurement device according to the first embodiment. FIG. 2(A) is an external perspective view of the gas concentration measurement device according to the first embodiment, and FIG. 2(B) is an exploded perspective view of the gas concentration measurement device according to the first embodiment.

Figure 3:
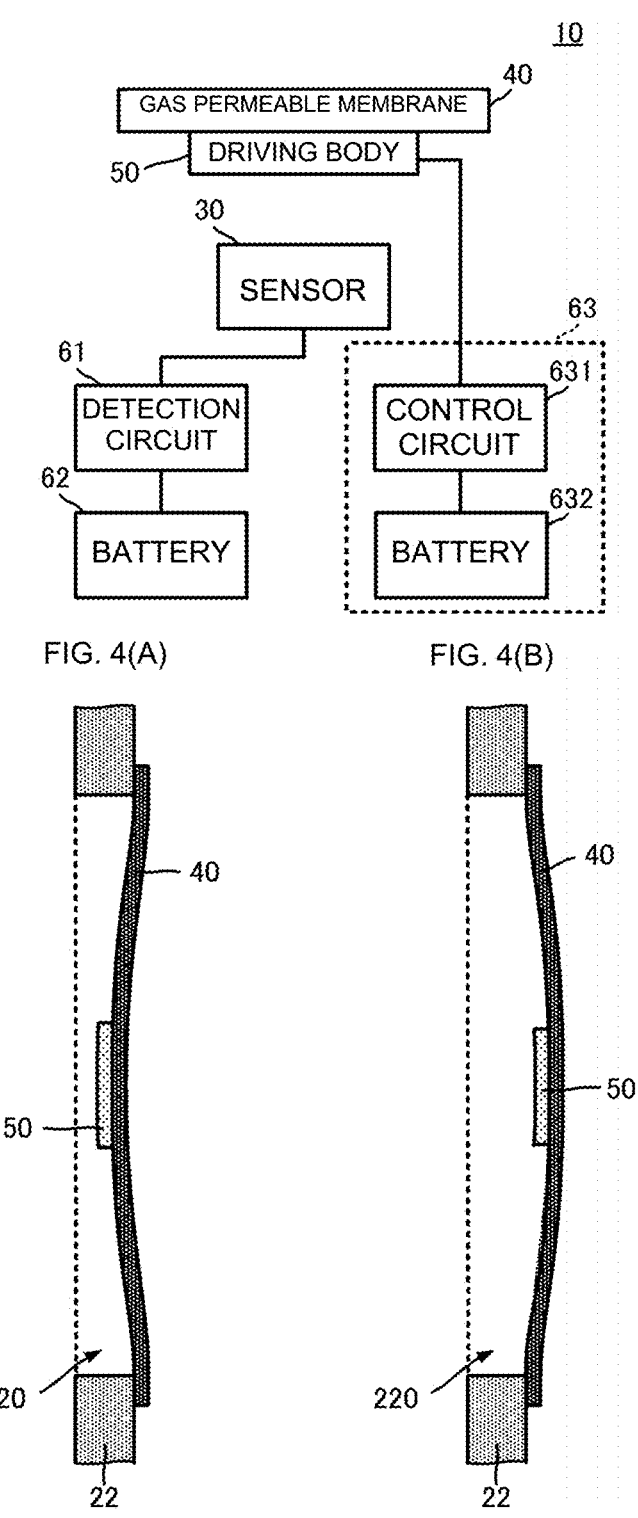
FIG. 3 is a functional block diagram of the gas concentration measurement device according to the first embodiment.

FIG. 3 is a functional block diagram of the gas concentration measurement device according to the first embodiment.

As illustrated in FIGS. 1, 2(A), 2(B), and 3, a gas concentration measurement device 10 includes a housing 20, a measurement instrument 30, a gas permeable membrane 40, a driving body 50, a detection circuit 61, a battery 62, and a driving device 63.

(Housing 20)

In the present embodiment, the housing 20 has an internal space 200 surrounded by six walls. For example, the housing 20 is composed of a box body 21 and a flat plate 22. The box body 21 has a recess surrounded by five walls. The internal space 200 of the housing 20 is formed by covering the recess in the box body 21 with the flat plate 22.

The flat plate 22 has a opening 220. The opening 220 has a circular shape when viewed in a direction orthogonal to the flat plate 22, and extends through the flat plate 22 in the thickness direction.

Thus, the opening 220 enables communication between the internal space 200 of the housing 20 and the outside of the housing 20.

The walls of the housing 20 (the box body 21 and the flat plate 22) are formed of a waterproof material (material that does not allow permeation of moisture). In this case, the walls of the housing 20 are preferably composed of a highly anticorrosive material. For example, the walls of the housing 20 may be formed of a metal, such as aluminum or stainless steel, or a polymeric material.

(Gas Permeable Membrane 40 and Driving Body 50)

The gas permeable membrane 40 is a membrane that allows passage of gas (gas to be measured) and substantially blocks passage of moisture. For example, the gas permeable membrane 40 is a membrane made of a porous polymeric film (e.g., expanded PTFE) or an amorphous polymeric film (e.g., amorphous fluoropolymer). The gas permeable membrane 40 preferably has a thickness of 150 μm or less. The phrase "substantially blocks passage of moisture" does not mean that the passage of moisture is 100% blocked, and passage of a very small amount of moisture is allowed within a practical range.

The gas permeable membrane 40 is disposed at the opening 220 in the housing 20. More specifically, the gas permeable membrane 40 is disposed to cover the opening 220. The gas permeable membrane 40 is fixed to the outer surface of the flat plate 22.

Since the gas permeable membrane 40 covers the opening 220 in the housing 20 as described above, gas can move between the internal space 200 of the housing 20 and the outside of the housing 20 while moisture is prevented from entering the internal space 200 of the housing 20.

The driving body 50 is capable of taking a plurality of shapes when energized or heated. The driving body 50 may be configured to generate vibrations. For example, the driving body 50 may be a piezoelectric body, a bimetal, or a shape-memory alloy.

The driving body 50 is disposed on the gas permeable membrane 40. The driving body 50 is disposed to overlap a portion of the gas permeable membrane 40. More specifically, in the case of FIGS. 1, 2(A), and 2(B), the driving body 50 is a circular plate-shaped piezoelectric body. The driving body 50 is disposed at the center of the gas permeable membrane 40 so that circular surfaces thereof are parallel to flat surfaces of the gas permeable membrane 40. The driving body 50 may be disposed directly on the gas permeable membrane 40. Alternatively, another member capable of transmitting stress from the driving body 50 to the gas permeable membrane 40 may be disposed between the driving body 50 and the gas permeable membrane 40.

Since the shape of the driving body 50 in plan view (circular shape) is smaller than the shape of the gas permeable membrane 40 in plan view, the driving body 50 covers only a portion of the gas permeable membrane 40. Therefore, the gas permeability is maintained in other regions of the gas permeable membrane 40.

The shape of the driving body 50 changes in response to a driving control signal (described in detail below) from a control circuit 631. For example, in FIGS. 1, 2(A), and 2(B), the driving body 50 expands and contracts in a direction substantially parallel to the flat surfaces of the gas permeable membrane 40 in response to the driving control signal.

The stress generated by the expansion and contraction of the driving body 50 is applied to the gas permeable membrane 40 on which the driving body 50 is disposed. Thus, the gas permeable membrane 40 expands and contracts, vibrating accordingly.

FIGS. 4(A) and 4(B) are enlarged side sectional views of the gas permeable membrane during vibration. As illustrated in FIG. 4(A), when the driving body 50 expands, the gas permeable membrane 40 curves convexly toward the side on which the driving body 50 is disposed. As illustrated in FIG. 4(B), when the driving body 50 contracts, the gas permeable membrane 40 curves convexly toward the side opposite to the side on which the driving body 50 is disposed.

When the driving body 50 repeatedly expands and contracts in response to the driving control signal, the gas permeable membrane 40 vibrates such that the central portion thereof move in a direction orthogonal to the flat surfaces of the gas permeable membrane 40.

The ratio of the area in which the driving body 50 overlaps the gas permeable membrane 40 is determined as appropriate based on the efficiency with which the driving body 50 vibrates the gas permeable membrane 40 (ratio of the magnitude of stress applied to the gas permeable membrane 40 by the driving body 50 to the driving energy supplied to the driving body 50) and the efficiency with which the gas permeates through the gas permeable membrane 40 (gas permeation rate per unit time).

(Measurement Instrument 30, Detection Circuit 61, Battery 62, and Driving Device 63)

The measurement instrument 30, the detection circuit 61, the battery 62, and the driving device 63 are disposed in the housing 20, that is, in the internal space 200 of the housing 20. A wiring conductor 281, a wiring conductor 282, a circuit board 291, and a circuit board 292 are also disposed in the internal space 200 of the housing 20.

The measurement instrument 30 includes a sensor case 31, a light source 32, an infrared sensor 33, and an optical filter 34.

The sensor case 31 is a box body and has an internal space 300. The sensor case 31 is smaller than the housing 20. One wall of the sensor case 31 has a opening 320. The opening 320 has a circular shape when viewed in a direction orthogonal to the wall in which the opening 320 is formed, and extends through this wall in the thickness direction.

Thus, the internal space 300 of the sensor case 31 communicates with the outside of the sensor case 31, that is, the internal space 200 of the housing 20 through the opening 320.

The light source 32, the infrared sensor 33, and the optical filter 34 are disposed in the sensor case 31 (in the internal space 300).

More specifically, the light source 32 is disposed on one of the walls of the sensor case 31 that is orthogonal to the wall in which the opening 320 is formed. The infrared sensor 33 is disposed on the wall of the sensor case 31 that faces the wall on which the light source 32 is disposed. The infrared sensor 33 has a light-receiving surface that faces the light source 32.

The optical filter 34 covers the light-receiving surface of the infrared sensor 33. The optical filter 34 is a filter that transmits infrared light but blocks light of other frequencies.

The measurement instrument 30 having the above-described structure constitutes a carbon dioxide measurement sensor using the non-dispersive infrared (NDIR) absorption method. In other words, the measurement instrument 30 outputs a measurement signal corresponding to the concentration of carbon dioxide in the internal space 300. The measurement instrument 30 is not limited to a carbon dioxide measurement sensor using the non-dispersive infrared (NDIR) absorption method.

The measurement instrument 30 is mounted on the circuit board 292, which is fixed to the housing 20. The measurement instrument 30 is disposed such that the sensor opening 320 in the sensor case 31 faces the opening 220 in the housing 20.

The detection circuit 61 includes a plurality of electronic circuit components 611. The detection circuit 61 is connected to the measurement instrument 30 by the wiring conductor 281. The detection circuit 61 determines the carbon dioxide concentration based on the measurement signal output by the measurement instrument 30, and generates carbon dioxide concentration detection data.

The carbon dioxide concentration detection data is stored in, for example, a storage medium included in the detection circuit 61. Thus, the carbon dioxide concentration detection data can be checked after the gas concentration measurement device 10 is collected.

The battery 62 supplies electric power to the measurement instrument 30 and the detection circuit 61.

As illustrated in FIG. 3, the driving device 63 includes the control circuit 631 and a battery 632. The battery 632 supplies electric power to the control circuit 631.

The control circuit 631 includes an electronic component, such as an IC. The control circuit 631 receives electric power from the battery 632 and generates a driving control signal for the driving body 50. The control circuit 631 outputs the driving control signal to the driving body 50. The driving control signal is an alternating current signal, such as a sine wave or a square wave.

The control circuit 631 of the driving device 63 is connected to the driving body 50 by the wiring conductor 282. Thus, the control circuit 631 supplies the driving control signal to the driving body 50 through the wiring conductor 282.

The detection circuit 61, the battery 62, and the driving device 63 are mounted on the circuit board 291, which is fixed to the housing 20.

The circuit board 291 and the circuit board 292 are connected to each other by the wiring conductor 281. The wiring conductor 281 enables the supply of electric power to the measurement instrument 30 and the transmission of the measurement signal from the measurement instrument 30 to the detection circuit 61.

(Mode of Use of Gas Concentration Measurement Device 10)

Figure 5:
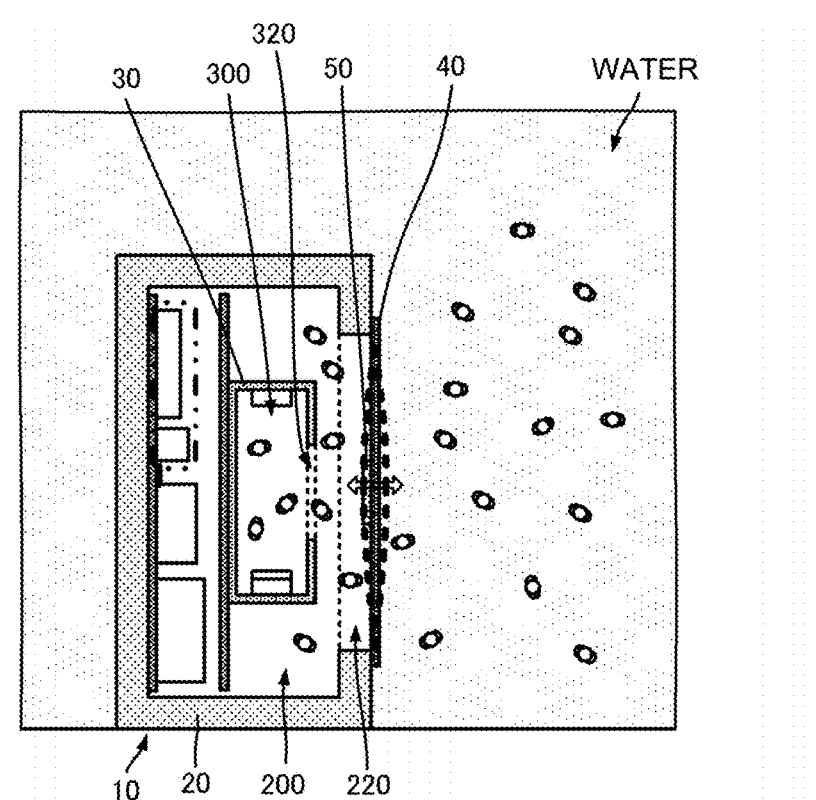
FIG. 5 is a side sectional view illustrating an example of the gas concentration measurement device in use.

FIG. 5 is a side sectional view illustrating an example of the gas concentration measurement device in use. As illustrated in FIG. 5, the gas concentration measurement device 10 is placed in the water in which gas to be measured is dissolved. Since the opening 220 in the housing 20 is covered by the gas permeable membrane 40 as described above, the internal space 200 of the housing 20 is sealed from moisture. Therefore, moisture is prevented from entering the internal space 200 of the gas concentration measurement device 10.

The internal space 200 of the housing 20 and the water are separated from each other by the gas permeable membrane 40. Therefore, gas is movable between the water and the internal space 200 of the housing 20. A vapor-liquid equilibrium state is reached between the water and the internal space 200 of the housing 20 in a certain time depending on the gas permeability of the gas permeable membrane 40.

Henry's law states that when a dilute solution containing volatile solutes is in equilibrium with the gas phase, the partial pressures of the solutes in the gas phase are proportional to the concentrations of the solutes in the solution. Therefore, when the internal space 200 of the housing 20 and the water are in the vapor-liquid equilibrium state, the gas concentrations in the internal space 200 are theoretically equal to the gas concentrations in the water.

Based on this theory, in the gas concentration measurement device 10, the measurement instrument 30 is disposed in the internal space 200 of the housing 20 and used to measure the carbon dioxide concentration in the internal space 200. Thus, the gas concentration measurement device 10 can measure the carbon dioxide concentration in the water.

In the gas concentration measurement device according to the related art, in which the gas permeable membrane is not vibrated, it takes a long time to reach the vapor-liquid equilibrium state after the gas concentration measurement device is immersed in the water. Therefore, the gas concentration measurement device cannot easily measure the carbon dioxide concentration in the water in a short time.

However, in the gas concentration measurement device 10, the driving body 50 vibrates the gas permeable membrane 40, so that the efficiency with which gas (carbon dioxide) moves through the gas permeable membrane 40 can be increased. Accordingly, in the gas concentration measurement device 10, the vapor-liquid equilibrium state is reached in a shorter time.

Figure 6:
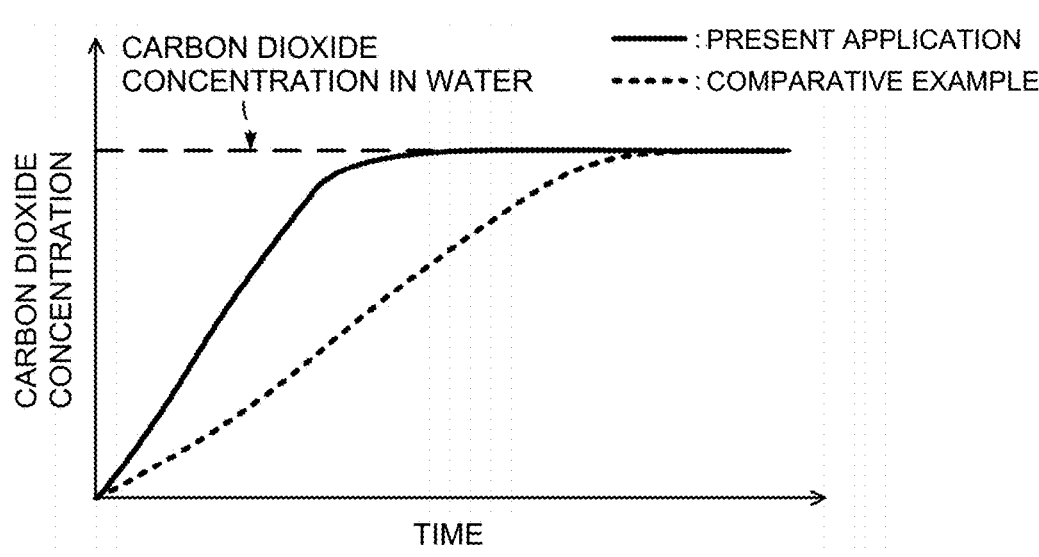
FIG. 6 is a graph showing an example of the change in the carbon dioxide concentration in an internal space of a housing in each of the structures of the present application and a comparative example.

FIG. 6 is a graph showing an example of the change in the carbon dioxide concentration in the internal space of the housing in each of the structures of the present application and a comparative example. In FIG. 6, the solid line represents the characteristics of the structure of the present application, and the dotted line represents the characteristics of the structure of the comparative example. In the structure of the comparative example, a gas permeable membrane having the same area and the same gas permeability as those in the structure of the present application is used, but is not vibrated.

As is clear from FIG. 6, according to the structure of the present application, the carbon dioxide concentration in the internal space 200 of the housing 20 reaches the carbon dioxide concentration in the water in a shorter time than in the structure of the comparative example.

Thus, the gas concentration measurement device 10 can quickly and easily measure the carbon dioxide concentration in the water.

In addition, according to this structure, the volume of the housing 20 may be as small as, for example, about 10 $cm^3$ to about 100 $cm^3$. In other words, the gas concentration measurement device 10 can be significantly smaller than the structure of the related art including a tank or the like.

In addition, although the area of the gas permeable membrane 40 is reduced as a result of the reduction in the size of the housing 20, a reduction in the gas permeation efficiency of the gas permeable membrane 40 can be suppressed due to the vibration.

Thus, the gas concentration measurement device 10 can be reduced in size, and can quickly and easily measure the carbon dioxide concentration in the water.

In the above-described structure, the driving body 50 is disposed directly on the gas permeable membrane 40. However, instead of being disposed directly on the gas permeable membrane 40, the driving body 50 may indirectly vibrate the gas permeable membrane 40 with, for example, another member provided therebetween. However, when the driving body 50 is disposed directly on the gas permeable membrane 40, the driving body 50 serves as a support for the gas permeable membrane 40. This prevents the gas permeable membrane 40 from tearing or otherwise breaking during vibration of the gas permeable membrane 40. The driving body 50 may be connected directly to the gas permeable membrane 40. However, instead of being connected directly to the gas permeable membrane 40, the driving body 50 may indirectly vibrate the gas permeable membrane 40 with, for example, another member provided therebetween.

The driving control signal may be supplied to the driving body 50 either before the gas concentration measurement device 10 is placed in the water or after the gas concentration measurement device 10 is placed in the water. When the gas concentration measurement device 10 is placed in the water, the timing and duration of the supply of the driving control signal to the driving body 50 can be set by setting, for example, the driving start time (time after the gas concentration measurement device 10 is activated or immersed in the water) and the driving time. Thus, the gas concentration measurement device 10 placed in the water can vibrate the gas permeable membrane 40 at a suitable time in the water.

Alternatively, the housing 20 may be equipped with an ultrasonic receiving sensor or the like, and the supply of the driving control signal to the driving body 50 may be externally controlled using ultrasonic waves. Alternatively, the housing 20 may be equipped with a water pressure sensor or the like, and the supply of the driving control signal to the driving body 50 may be controlled based on a detection value obtained by the water pressure sensor.

Figure 7:
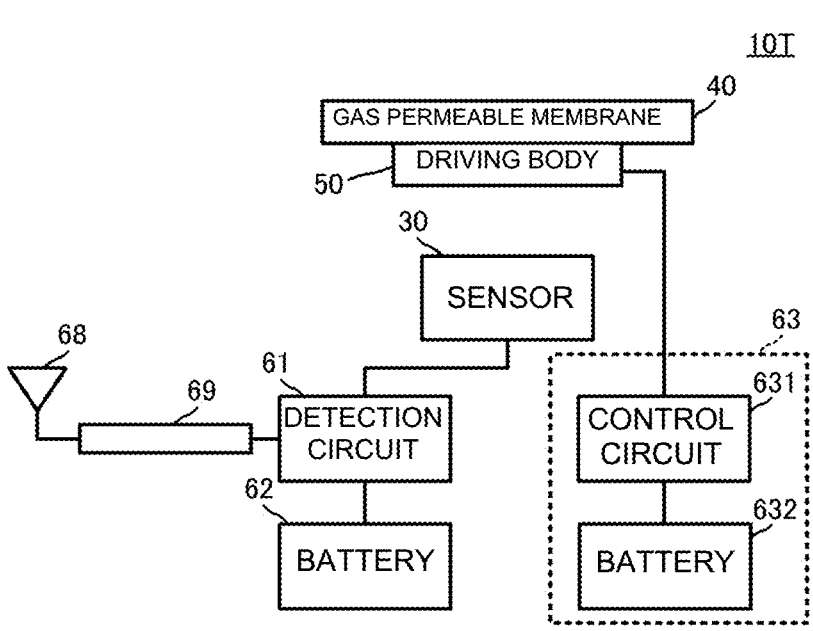
FIG. 7 is a functional block diagram of a gas concentration measurement device having a function of transmitting detection data.

The detection data may be transmitted to the outside. FIG. 7 is a functional block diagram of a gas concentration measurement device having a function of transmitting the detection data. As illustrated in FIG. 7, a gas concentration measurement device 10T having a function of transmitting detection data includes an antenna 68 and a communication cable 69 in addition to the above-described gas concentration measurement device 10.

When, for example, the gas concentration measurement device 10T is used in the water (similarly to FIG. 5), the antenna 68 is disposed in a buoy or the like that floats on the water surface. The communication cable 69 is waterproof. The communication cable 69 connects the antenna 68 and the detection circuit 61 to each other. The detection circuit 61 outputs the detection data (detection data based on the measurement signal representing the concentration of the gas) to the antenna 68 through the communication cable 69. The antenna 68 wirelessly transmits the detection data to an external analysis device or the like. The method for transmitting detection data is not limited to this.

Second Embodiment

Figure 8:
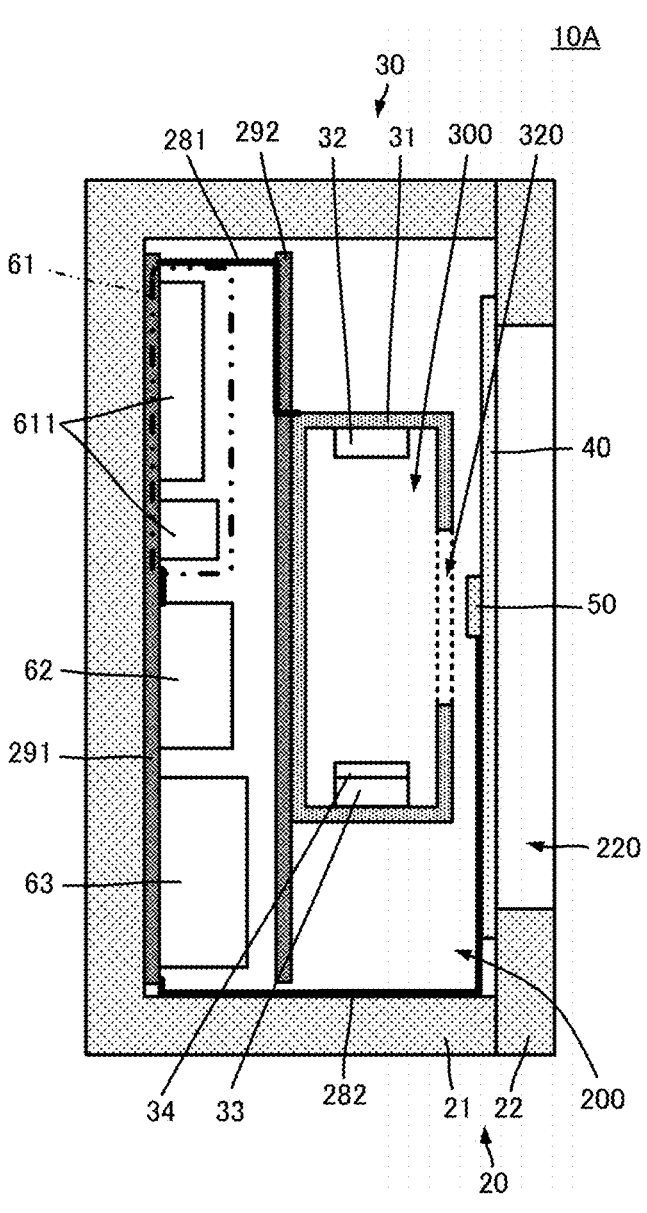
FIG. 8 is a sectional view illustrating the structure of a gas concentration measurement device according to a second embodiment.

A gas concentration measurement device according to a second embodiment of the present disclosure will now be described with reference to the drawings. FIG. 8 is a sectional view illustrating the structure of the gas concentration measurement device according to the second embodiment.

As illustrated in FIG. 8, the gas concentration measurement device 10A according to the second embodiment differs from the gas concentration measurement device 10 according to the first embodiment in the manner in which the gas permeable membrane 40 is disposed on the housing 20. Other structures of the gas concentration measurement device 10A are similar to those of the gas concentration measurement device 10, and description of similar parts is omitted.

In the gas concentration measurement device 10A, the gas permeable membrane 40 is disposed on a surface of the flat plate 22 of the housing 20 facing the internal space 200.

According to this structure, similarly to the gas concentration measurement device 10, the gas concentration measurement device 10A can be reduced in size, and can quickly and easily measure the carbon dioxide concentration in the water.

In the gas concentration measurement device 10A, a joining portion between the gas permeable membrane 40 and the housing 20 is disposed inside the housing 20. Therefore, when the gas concentration measurement device 10A is immersed in the water, the joining portion between the gas permeable membrane 40 and the housing 20 does not easily come into contact with an external foreign object and cause separation thereof.

Third Embodiment

Figure 9:
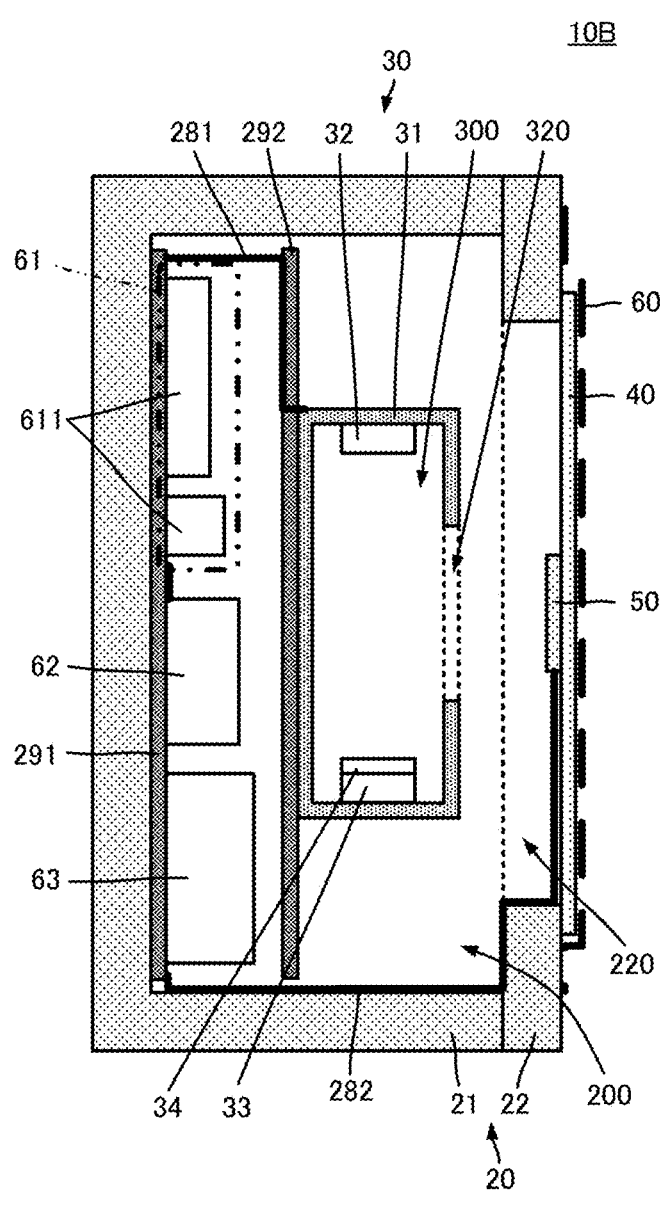
FIG. 9 is a sectional view illustrating the structure of a gas concentration measurement device according to a third embodiment.
Figure 10:
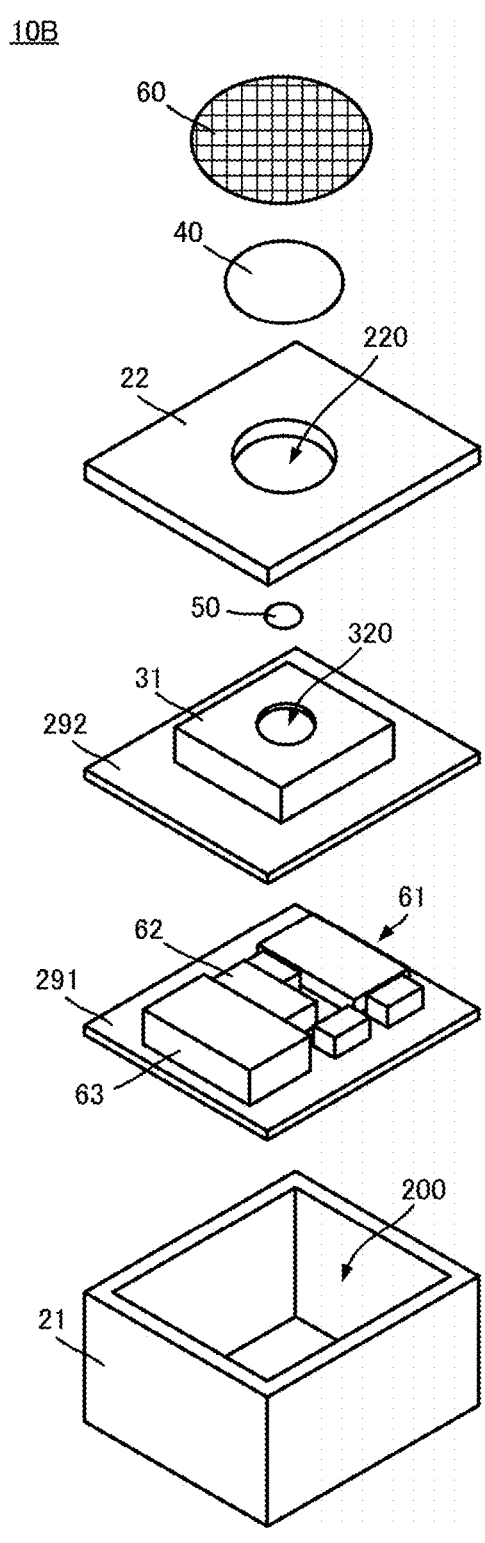
FIG. 10 is an exploded perspective view of the gas concentration measurement device according to the third embodiment.

A gas concentration measurement device according to a third embodiment of the present disclosure will now be described with reference to the drawings. FIG. 9 is a sectional view illustrating the structure of the gas concentration measurement device according to the third embodiment. FIG. 10 is an exploded perspective view of the gas concentration measurement device according to the third embodiment.

As illustrated in FIGS. 9 and 10, the gas concentration measurement device 10B according to the third embodiment differs from the gas concentration measurement device 10 according to the first embodiment in that a mesh material 60 is additionally provided. Other structures of the gas concentration measurement device 10B are similar to those of the gas concentration measurement device 10, and description of similar parts is omitted.

The mesh material 60 may be made of, for example, stainless steel or aluminum. The mesh material 60 may be a flat plate having a plurality of holes, such as perforated metal.

The mesh material 60 is disposed to cover the outer surface of the gas permeable membrane 40.

According to this structure, similarly to the gas concentration measurement device 10, the gas concentration measurement device 10B can be reduced in size, and can quickly and easily measure the carbon dioxide concentration in the water.

In addition, in the gas concentration measurement device 10B, due to the mesh material 60, the gas permeable membrane 40 does not easily come into contact with an external foreign object and break.

[Various Forms of Driving Bodies]

FIGS. 11(A), 11(B), 11(C), and 11(D) are plan views illustrating various forms of driving bodies.

Figures 11A, 11B, 11C, 11D:
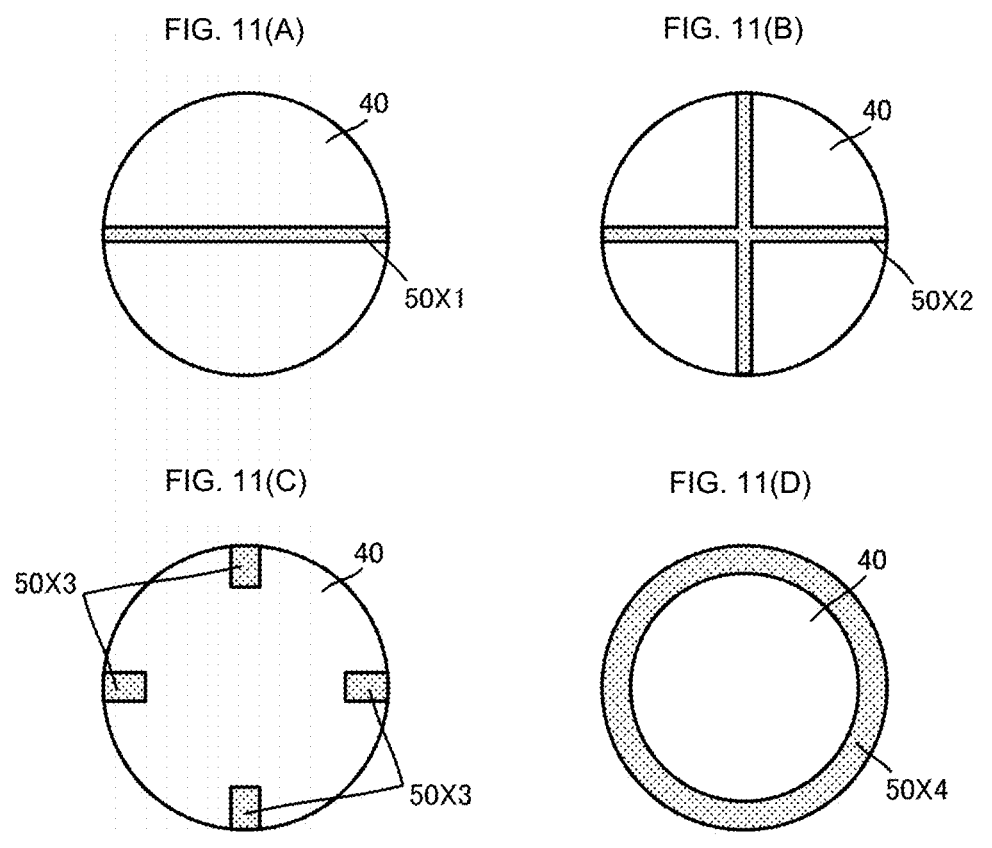

In FIG. 11(A), a driving body 50X1 is a flat strip-shaped body (having a shape with a longitudinal direction). The driving body 50X1 extends in a diameter direction of the gas permeable membrane 40. The driving body 50X1 expands and contracts in the longitudinal direction. The driving body 50X1 is preferably made of, for example, piezoelectric ceramics, polylactic acid, or bimetal.

In FIG. 11(B), a driving body 50X2 is composed of two flat strip-shaped bodies (having a shape with a longitudinal direction). The two strip-shaped bodies are orthogonal to each other, and each extend in a diameter direction of the gas permeable membrane 40. The two strip-shaped bodies of the driving body 50X2 expand and contract in the longitudinal directions thereof. The driving body 50X2 is preferably made of, for example, piezoelectric ceramics, polylactic acid, or bimetal.

In FIG. 11(C), a driving body 50X3 includes a plurality of individual driving bodies. The individual driving bodies have a rectangular shape in plan view. The individual driving bodies are arranged in a circumferential direction of the gas permeable membrane 40 with predetermined intervals therebetween. The intervals between the individual driving bodies are preferably equal, but it is not necessary that the intervals be equal. The number of individual driving bodies is not limited to four. Each individual driving body expands and contracts in a direction parallel to a direction from an outer end of the gas permeable membrane 40 at which the individual driving body is disposed toward the center of the gas permeable membrane 40.

In FIG. 11(D), a driving body 50X4 expands and contracts in the longitudinal direction thereof. The driving body 50X4 is preferably made of polylactic acid or bimetal. The driving body 50X4 is a flat annular membrane. The driving body 50X4 extends along the outer periphery of the gas permeable membrane 40. The driving body 50X4 expands and contracts in the circumferential direction.

The above-described driving bodies 50X1, 50X2, 50X3, and 50X4 are examples, and may be combined with each other. In other words, the driving body is not limited to the above-described structures as long as the driving body is disposed on the gas permeable membrane 40 and is capable of vibrating the gas permeable membrane 40.

In the above description, the driving body is disposed on a side of the gas permeable membrane 40 facing the internal space 200. However, the driving body may be disposed on the outer surface (surface opposite to the surface facing the internal space 200) of the gas permeable membrane 40. Also, the driving body may be disposed on each surface of the gas permeable membrane 40.

[Various Forms of Housings and Gas Permeable Membranes]

Figure 12C:
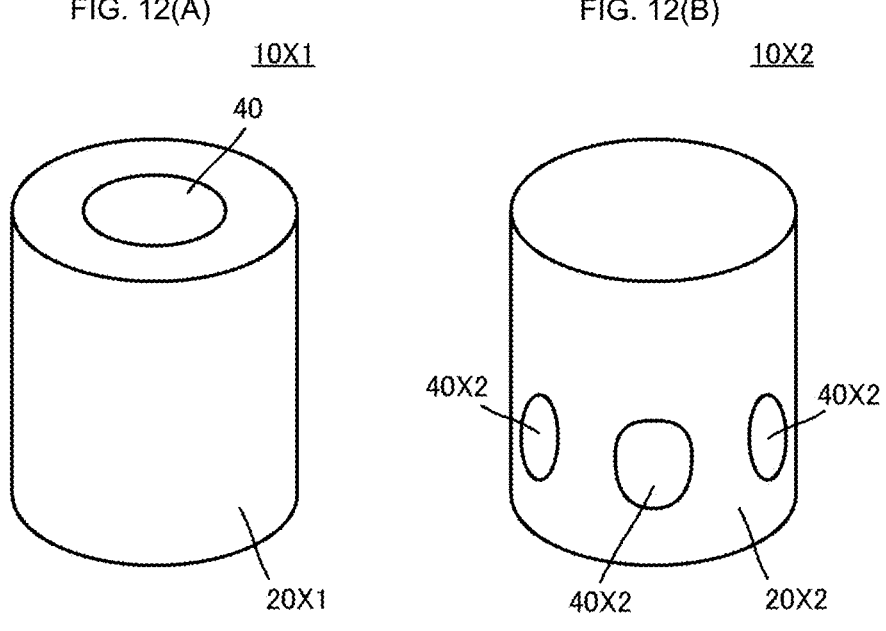

FIGS. 12(A), 12(B), and 12(C) are plan views illustrating various forms of housings and gas permeable membranes.

In FIG. 12(A), a gas concentration measurement device 10X1 includes a cylindrical housing 20X1. The gas permeable membrane 40 is disposed on an end surface of the housing 20X2 orthogonal a peripheral surface of the housing 20X2.

In FIG. 12(B), a gas concentration measurement device 10X2 includes a cylindrical housing 20X2. Plural gas permeable membranes 40X2 are disposed on a peripheral surface of the housing 20X2.

In FIG. 12(C), a gas concentration measurement device 10X3 includes a gas permeable membrane 40X3 having a rectangular shape in plan view.

Thus, in the gas concentration measurement device, the shape of the housing, the shape of the gas permeable membrane in plan view, the position of the gas permeable membrane on the housing, and the number of gas permeable membranes may be set as appropriate.

The above-described embodiments and various forms may be combined as appropriate, and an operational effect corresponding to each combination may be obtained.

<1> A gas concentration measurement device including: a waterproof housing including a wall that defines an internal space, the wall including an opening communicating between the internal space and an outside of the housing; a measurement instrument in the internal space, the measurement instrument constructed to measure a concentration of a gas; a gas permeable membrane covering the opening, the gas permeable membrane allowing passage of the gas and substantially blocking passage of moisture; and a driving body constructed to vibrate the gas permeable membrane.

<2> The gas concentration measurement device according to <1>, wherein the driving body is constructed so as to take a plurality of shapes when energized or heated.

<3> The gas concentration measurement device according to <2>, wherein the driving body is a piezoelectric body.

<4> The gas concentration measurement device according to <2>, wherein the driving body is a bimetal.

<5> The gas concentration measurement device according to any one of <1> to <4>, wherein the driving body is on a side of the gas permeable membrane facing the internal space.

<6> The gas concentration measurement device according to any one of <1> to <5>, wherein the driving body is film-shaped.

<7> The gas concentration measurement device according to any one of <1> to <6>, wherein the driving body is on the gas permeable membrane.

<8> The gas concentration measurement device according to <7>, wherein the driving body is constructed as a support for the gas permeable membrane.

<9> The gas concentration measurement device according to any one of <1> to <8>, wherein the gas permeable membrane and the driving body are on a side of the opening facing the internal space.

<10> The gas concentration measurement device according to any one of <1> to <9>, further including: a control circuit that controls vibration of the driving body, wherein the control circuit is constructed to drive the driving body (1) such that the gas permeable membrane does not project toward the outside of the housing beyond a position of the gas permeable membrane in a non-vibrating state, or (2) such that the gas permeable membrane vibrates greater toward the internal space than toward the outside of the housing with respect to the position of the gas permeable membrane in the non-vibrating state.

<11> The gas concentration measurement device according to <10>, further including: a first power supply that supplies electricity to the measurement instrument and a second power supply that supplies electricity to the control circuit, wherein the first power supply and the second power supply are in the internal space.

<12> The gas concentration measurement device according to any one of <1> to <10>, further including: a power supply that supplies electricity to the measurement instrument, the power supply located in the internal space.

<13> The gas concentration measurement device according to any one of <1> to <12>, further including: an antenna constructed to transmit detection data based on a measurement signal representing the concentration of the gas to an outside of the gas concentration measurement device.

REFERENCE SIGNS LIST 10, 10A, 10B, 10T, 10X1, 10X2, 10X3 gas concentration measurement device
20, 20X1, 20X2 housing
21 box body
22 flat plate
30 measurement instrument
31 sensor case
32 light source
33 infrared sensor
34 optical filter
40, 40X2, 40X3 gas permeable membrane
50, 50X1, 50X2, 50X3, 50X4 driving body
60 mesh material
61 detection circuit
62 battery
63 driving device
68 antenna
69 communication cable
200 internal space
220 opening
281, 282 wiring conductor
291, 292 circuit board
300 internal space
320 opening
611 electronic circuit component
631 control circuit
632 battery

The invention claimed is:

1. A gas concentration measurement device comprising: a waterproof housing including a wall that defines an internal space, the wall including an opening communicating between the internal space and an outside of the housing; a measurement instrument in the internal space, the measurement instrument constructed to measure a concentration of a gas; a gas permeable membrane covering the opening, the gas permeable membrane allowing passage of the gas and substantially blocking passage of moisture; and a driving body constructed to vibrate the gas permeable membrane.

2. The gas concentration measurement device according to claim 1, wherein the driving body is constructed so as to take a plurality of shapes when energized or heated.

3. The gas concentration measurement device according to claim 2, wherein the driving body is a piezoelectric body.

4. The gas concentration measurement device according to claim 2, wherein the driving body is a bimetal.

5. The gas concentration measurement device according to claim 1, wherein the driving body is on a side of the gas permeable membrane facing the internal space.

6. The gas concentration measurement device according to claim 1, wherein the driving body is film-shaped.

7. The gas concentration measurement device according to claim 1, wherein the driving body is on the gas permeable membrane.

8. The gas concentration measurement device according to claim 7, wherein the driving body is constructed as a support for the gas permeable membrane.

9. The gas concentration measurement device according to claim 1, wherein the gas permeable membrane and the driving body are on a side of the opening facing the internal space.

10. The gas concentration measurement device according to claim 1, further comprising: a control circuit that controls vibration of the driving body, wherein the control circuit is constructed to drive the driving body (1) such that the gas permeable membrane does not project toward the outside of the housing beyond a position of the gas permeable membrane in a non-vibrating state, or (2) such that the gas permeable membrane vibrates greater toward the internal space than toward the outside of the housing with respect to the position of the gas permeable membrane in the non-vibrating state.

11. The gas concentration measurement device according to claim 10, further comprising: a first power supply that supplies electricity to the measurement instrument; and a second power supply that supplies electricity to the control circuit, wherein the first power supply and the second power supply are in the internal space.

12. The gas concentration measurement device according to claim 1, further comprising: a power supply that supplies electricity to the measurement instrument, the power supply located in the internal space.

13. The gas concentration measurement device according to claim 1, further comprising: an antenna constructed to transmit detection data based on a measurement signal representing the concentration of the gas to an outside of the gas concentration measurement device.

14. The gas concentration measurement device according to claim 1, wherein the wall of the housing is a metal or a polymeric material.

15. The gas concentration measurement device according to claim 1, wherein the gas permeable membrane comprises a porous polymeric film or an amorphous polymeric film.

16. The gas concentration measurement device according to claim 1, wherein the gas permeable membrane has a thickness of 150 μm or less.

17. The gas concentration measurement device according to claim 1, wherein the driving body is a circular plate-shaped piezoelectric body.

18. The gas concentration measurement device according to claim 1, wherein a shape of the driving body in a plan view is smaller than a shape of the gas permeable membrane in the plan view.

19. The gas concentration measurement device according to claim 1, wherein the measurement instrument comprises a carbon dioxide measurement sensor.

20. The gas concentration measurement device according to claim 1, wherein the driving body is at least one of a flat strip-shaped body that extends in a diameter direction of the gas permeable membrane, two flat strip-shaped bodies that are orthogonal to each other and each of which extend in the diameter direction of the gas permeable membrane, a plurality of individual driving bodies having a rectangular shape in a plan view and arranged in a circumferential direction of the gas permeable membrane with predetermined intervals therebetween, and a flat annular membrane that extends along an outer periphery of the gas permeable membrane.

* * * * *